(12) United States Patent
Nakagawa et al.

(10) Patent No.: US 10,051,882 B2
(45) Date of Patent: Aug. 21, 2018

(54) BASIS WEIGHT MEASURING APPARATUS AND METHOD FOR SHEET TOBACCO, AND MANUFACTURING SYSTEM AND METHOD FOR SHEET TOBACCO

(71) Applicant: JAPAN TOBACCO INC., Tokyo (JP)

(72) Inventors: Seiji Nakagawa, Tokyo (JP); Kazuhiro Tokuda, Tokyo (JP); Kaoru Narazaki, Tokyo (JP); Tsutomu Kamishiraki, Tokyo (JP); Yasushige Tsuchiya, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 702 days.

(21) Appl. No.: 14/607,253

(22) Filed: Jan. 28, 2015

(65) Prior Publication Data

US 2015/0136161 A1  May 21, 2015

Related U.S. Application Data

(63) Continuation of application No. PCT/JP2012/069469, filed on Jul. 31, 2012.

(51) Int. Cl.
*A24B 3/14* (2006.01)
*D21G 9/00* (2006.01)
(Continued)

(52) U.S. Cl.
CPC ............. *A24B 3/14* (2013.01); *D21G 9/0009* (2013.01); *G01G 9/005* (2013.01); *G01G 17/02* (2013.01);
(Continued)

(58) Field of Classification Search
CPC .................................................. D21G 9/0009
See application file for complete search history.

(56) References Cited

U.S. PATENT DOCUMENTS 3,415,253 A * 12/1968 Michels ................. A24B 15/12
 131/373
6,198,537 B1    3/2001 Bokelman et al.

FOREIGN PATENT DOCUMENTS

JP           3216953 B2    10/2001
WO     WO 99/02976 A1     1/1999
WO   WO 2010/041660 A1    4/2010

OTHER PUBLICATIONS

Isokangas et al., Analysis of formation and floc size on the basis of optical transmittance, Jun. 2011, University of Oulu.*
(Continued)

*Primary Examiner* — Anthony J Calandra
(74) *Attorney, Agent, or Firm* — Birch, Stewart, Kolasch & Birch, LLP

(57) ABSTRACT

A measuring apparatus for performing a basis weight measuring method for sheet tobacco according to the present invention includes: a light source (28) that emits light to sheet tobacco (ST) passing through a measurement position (P) on a transport path (18); and a visual sensor (30), the visual sensor (30) having a color camera (32) disposed with the transport path (18) put between the color camera (32) and the light source (28), a processing part (40) that transforms a color image of the sheet tobacco (ST) taken by the camera (32) into a grayscale image, and a conversion part (42) that converts an average gray level of the grayscale image into a basis weight of the sheet tobacco (ST) with reference to a conversion map which indicates a relationship between the average gray level of the grayscale image and an actual basis weight of sheet tobacco (ST).

13 Claims, 8 Drawing Sheets

(51) Int. Cl.
*G01G 17/02* (2006.01)
*G01N 21/89* (2006.01)
*G01G 23/35* (2006.01)
*G06T 7/00* (2017.01)
*G01G 9/00* (2006.01)

(52) U.S. Cl.
CPC ......... *G01G 23/35* (2013.01); *G01N 21/8901* (2013.01); *G06T 7/0006* (2013.01); *G06T 2207/10024* (2013.01); *G06T 2207/30128* (2013.01)

(56) References Cited

OTHER PUBLICATIONS

Curtin Dennis, Image Sensors and Color, May 14, 2010 (downloaded from archive.org on Jan. 19, 2018).*
Lien et al., A method of Inspecting Non-woven Basis Weight using the Exponential Law of Absorption and Image processing, 2006, Textile Research Journal, vol. 76(7).*
Greenwood Instruments, AccuForm Tester, Nov. 29, 2010 (downloaded fro archive.org Jan. 19, 2018).*
European Office Action, dated Aug. 17, 2017, for European Application No. 12882414.1.

* cited by examiner

BASIS WEIGHT MEASURING APPARATUS AND METHOD FOR SHEET TOBACCO, AND MANUFACTURING SYSTEM AND METHOD FOR SHEET TOBACCO

CROSS REFERENCE TO RELATED APPLICATIONS

This non-provisional application is a continuation of International Application No. PCT/JP2012/069469 filed on Jul. 31, 2012. The entire content of the above application is hereby incorporated by reference into the present application.

TECHNICAL FIELD

The present invention relates to a measuring apparatus and a measuring method for measuring a basis weight of sheet tobacco, and also to a sheet tobacco manufacturing system and a sheet tobacco manufacturing method in which the measuring apparatus and the measuring method are incorporated, respectively.

BACKGROUND ART

Cigarettes contain not only cut tobacco obtained by cutting lamina tobacco, but also reconstructed cut tobacco obtained by cutting sheet tobacco as filling materials. For example, such sheet tobacco is formed by a forming machine described in Patent Document 1, and the forming machine includes an adjustment apparatus for adjusting the basis weight of the sheet tobacco.

The basis weight of the sheet tobacco determines the thickness of the reconstructed cut tobacco and thus greatly affects the taste of the cigarette. Therefore, the sheet tobacco manufactured by the forming machine is sampled at fixed time intervals. The weight of a sample is measured using a scale, and based on the result of the measurement, the basis weight of the sheet tobacco is calculated.

When the calculated basis weight falls out of a basis weight standard range required for the sheet tobacco, the adjustment apparatus in the forming machine is actuated so as to make the basis weight of the sheet tobacco fall within the standard range.

PRIOR ART DOCUMENT

Patent Document

Patent Document 1: Japanese Patent No. 3216953 (JP3216952 B2)

SUMMARY OF THE INVENTION

Problems to be Solved by the Invention

The aforementioned sheet tobacco sampling, sample weight measurement and sheet tobacco basis weight calculation are manually performed offline, requiring a long period of time from the sampling to the basis weight calculation. Therefore, production of inferior sheet tobacco is undesirably continued until the basis weight measurement result is reflected in the actuation of the adjustment apparatus in the forming machine.

A first object of the present invention is to provide a basis weight measuring apparatus and a basis weight measuring method capable of measuring a basis weight of sheet tobacco online. A second object of the present invention is to provide a sheet tobacco manufacturing system and a sheet tobacco manufacturing method that enable substantial reduction of production of inferior sheet tobacco using the basis weight measuring apparatus and method according to the present invention.

Means for Solving the Problems

The aforementioned first object is achieved by the basis weight measuring apparatus for sheet tobacco according to the present invention, and the basis weight measuring apparatus comprises:

a light source disposed on a transport path for the sheet tobacco, and emitting light toward the sheet tobacco passing through a measurement position defined in the transport path; and a visual sensor including a camera disposed with the transport path put between the visual sensor and the light source, the visual sensor measuring a basis weight of the sheet tobacco based on an image of the sheet tobacco taken by the camera when the sheet tobacco passes through the measurement position, and the visual sensor further includes:

a calculation section that calculates an average gray level of the image and outputs the average gray level; and a converter including a conversion map indicating a relationship between the average gray level and an actual measurement value obtained by actually measuring the basis weight of the sheet tobacco, the converter converting the average gray level into the basis weight of the sheet tobacco with reference to the conversion map.

According to the above-stated basis weight measuring apparatus, the basis weight of the sheet tobacco is immediately measured in the course of the transport of the sheet tobacco, that is, online, enabling the result of the measurement to be promptly reflected in production of the sheet tobacco.

For example, the camera may be a color camera that obtains the image of the sheet tobacco as a color image, and in this case, the calculation section includes a transformer that transforms the color image into a grayscale image, and calculates the average gray level based on the grayscale image.

The transport path includes an upstream section that transports the sheet tobacco toward the measurement position; and a downstream section disposed with a clearance, in which the measurement position is defined, interposed between the downstream section and a downstream end of the upstream section, the downstream section transporting the sheet tobacco passing through the measurement position; and the light source and the camera are disposed with the clearance put therebetween.

For example, the transport path can further include a transport guide plate disposed in the clearance, and guiding the transport of the sheet tobacco when the sheet tobacco moves from the upstream section toward the downstream section through the measurement position; and an aperture formed in the transport guide plate, and allowing the sheet tobacco passing through the measurement position to be exposed to the light source, and the aperture has an axis perpendicular to the transport guide plate.

The transport guide plate maintains a fixed distance between the camera and the sheet tobacco at the measurement position, and thereby contributes to more correct basis weight calculation for the sheet tobacco.

If the sheet tobacco is a rolled sheet tobacco, it is preferable that the camera is disposed on the axis of the aperture while the light source is disposed to deviate from the aperture in a direction along the transport path or a direction across the transport path. It is more preferable that the light source has an optical axis inclined relative to the axis of the aperture.

With the aforementioned layout of the light source and the camera relative to the rolled sheet tobacco, even if small through holes are present in a distributed manner in the rolled sheet tobacco and light from the light source passes through these through holes, the passing light does not directly enter the camera. Therefore, the camera can obtain an image of the rolled sheet tobacco that is free from halation, and thus, based on the image, the basis weight measuring apparatus can measure a more correct basis weight of the rolled sheet tobacco.

The first object is achieved also by the measuring method according to the present invention, which corresponds to the above-stated basis weight measuring apparatus, and furthermore, the aforementioned second object is achieved by a sheet tobacco manufacturing system and method in which the basis weight measuring apparatus and method according to the present invention are incorporated, respectively. Details of the basis weight measuring method, the sheet tobacco manufacturing system and the sheet tobacco manufacturing method according to the present invention will be clarified from the accompanying drawings and the below description.

Advantageous Effects of the Invention

With the basis weight measuring apparatus and method for sheet tobacco according to the present invention, a basis weight of sheet tobacco can be measured in a course of transport of the sheet tobacco, that is, online, and thus the measured basis weight can promptly be reflected in production of the sheet tobacco.

Furthermore, the sheet tobacco manufacturing system and method in which the basis weight measuring apparatus and method are incorporated, respectively, enable the sheet tobacco to be manufactured while the basis weight of the sheet tobacco is maintained within a reference range, reducing production of inferior sheet tobacco.

MODE FOR CARRYING OUT THE INVENTION

Figure 1:
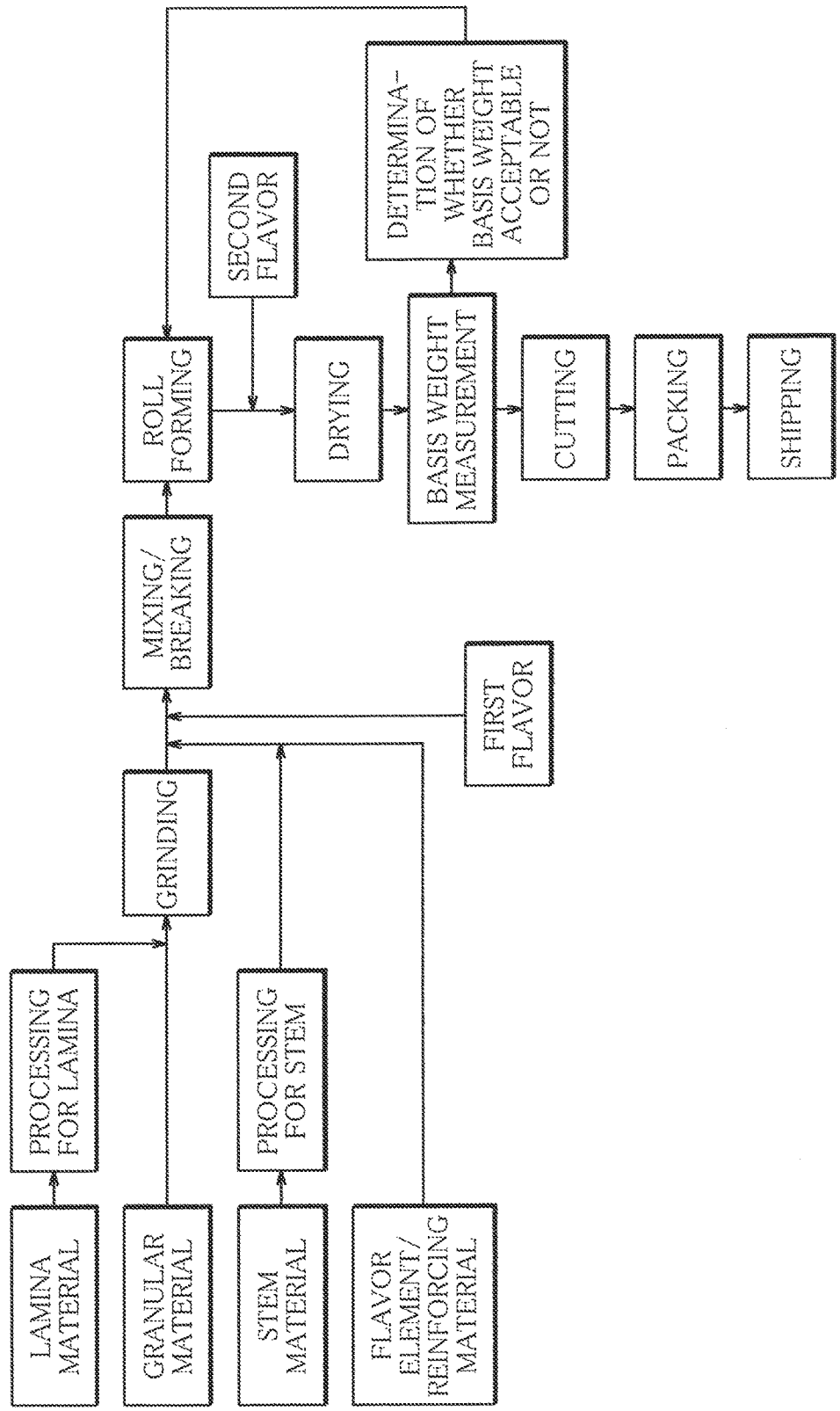
FIG. 1 is a block diagram schematically illustrating a sheet tobacco manufacturing system and a sheet tobacco manufacturing method according to an embodiment.

FIG. 1 schematically illustrates a manufacturing system from, for example, forming of rolled sheet tobacco (hereinafter simply referred to as "sheet tobacco") from ingredients to shipping of the sheet tobacco through basis weight measurement and basis weight control.

Sheet tobacco ingredients include a flavor element (cornstarch) and a reinforcing material in addition to lamina material obtained from leaf tobacco, granular material such as cut tobacco and recycled cut tobacco collected from a cigarette manufacturing process and stem material obtained from leaf tobacco.

The lamina material is subjected to processing for lamina and then added to the granular material, thereby forming first blend material. The processing for lamina includes cracking, humidity control and drying of the lamina material, and the granular material may be subjected to cracking processing before the addition of the lamina material. Subsequently, the first blend material is further ground.

Meanwhile, the stem material is subjected to processing for stem, and the processing for stem herein includes cracking, grinding, humidity control, flavor addition and drying of the stem. Subsequently, the stem material is added to the first blend material subjected to the grinding processing together with the flavor element and the reinforcing material, thereby forming second blend material. The reinforcing material may be subjected to cracking processing and grinding processing as necessary before the reinforcing material is added to the first blend material.

Subsequently, a first flavor is further added to the second blend material, and the second blend material and the first flavor are supplied to a blender. In the blender, water is added to the second blend material and the first flavor, and the second blend material and the first flavor are subjected to mixing/breaking processing, thereby forming fluid material.

The fluid material is formed into sheet tobacco by roll forming, and the sheet tobacco is subjected to processing for adding a second flavor and then dried in a drier. Subsequently, the sheet tobacco is shipped after basis weight measurement, cutting and packaging processing.

Meanwhile, based on a result of the basis weight measurement, whether a basis weight of the sheet tobacco is acceptable or not is determined, and a result of the determination is reflected in the roll forming.

Figure 2:
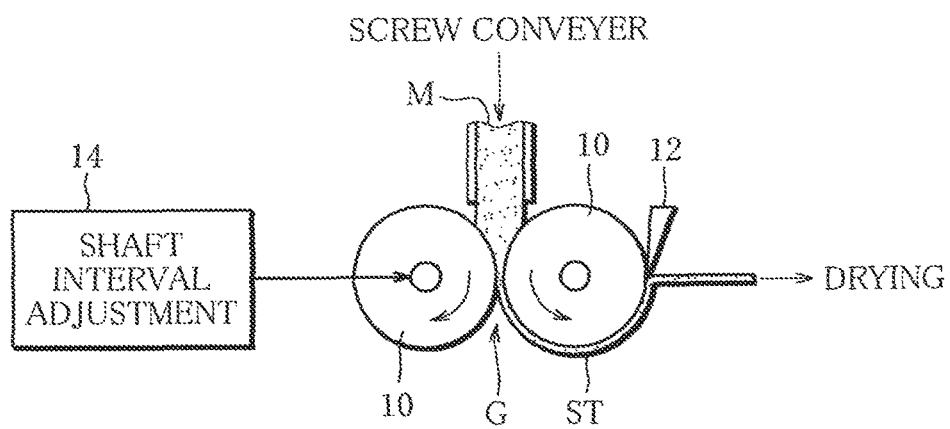
FIG. 2 is a schematic diagram illustrating a part of a roll forming machine for sheet tobacco, which is incorporated in the manufacturing system in FIG. 1.

FIG. 2 schematically illustrates a part of a roll forming machine for forming sheet tobacco.

The roll forming machine includes a pair of press rolls 10, and these press rolls 10 are horizontally disposed. A roll shaft of each press roll 10 is connected to a drive source (not illustrated), whereby the pair of press rolls 10 are rotatable in respective arrow directions in FIG. 2, which are opposite to each other. Here, a peripheral speed of one press roll 10 is slightly higher than that of the other press roll 10.

A gap G is secured between the press rolls 10, and fluid material M is quantitatively supplied to the gap G from above. For example, the fluid material M is supplied to a screw conveyer, and the screw conveyer includes an outlet disposed above the pair of press rolls 10.

Therefore, upon rotation of the pair of press rolls 10 in the respective directions opposite to each other while the fluid material M being supplied to the gap G, theses press rolls 10 push the fluid material M out of the gap G and thereby form the fluid material M into sheet tobacco ST. Here, since the sheet tobacco ST is formed in such a manner that the sheet tobacco ST is wound around the high speed-side press roll 10 from the gap G, and the high speed-side press roll 10 includes a scraper 12, and the scraper 12 removes the sheet tobacco ST from the high speed-side press roll 10. Subsequently, the removed sheet tobacco ST is dried as described above.

A thickness of the sheet tobacco ST is determined by the aforementioned gap G, and the roll forming machine further includes a shaft interval adjustment device 14 that adjusts a size of the gap G, that is, an interval between the roll shafts of the pair of press rolls 10. As is clear from FIG. 2, the shaft interval adjustment device 14 adjusts the gap G based on a result of the aforementioned determination of whether the basis weight is acceptable or not, and details of the adjustment here will be described later.

Figure 3:
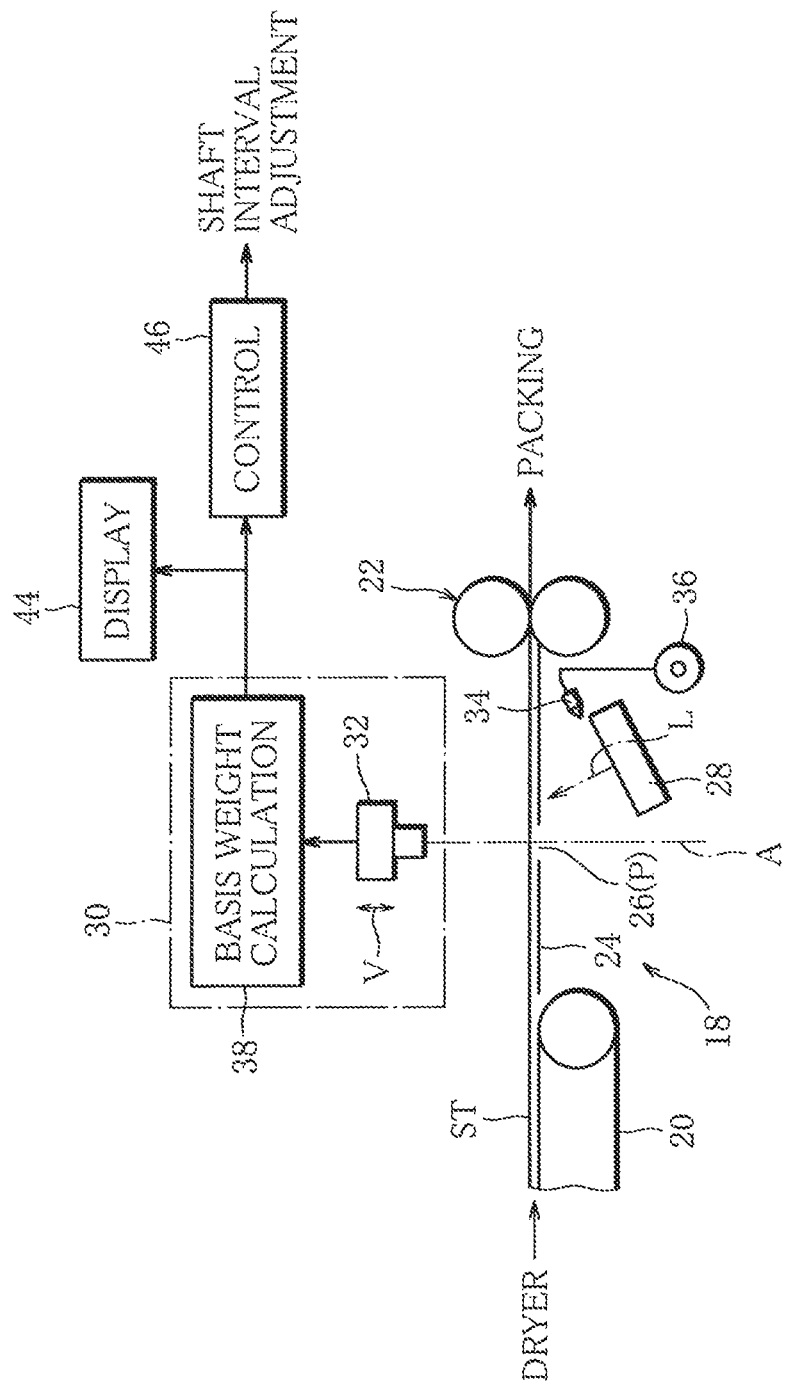
FIG. 3 is a schematic diagram illustrating a basis weight measuring apparatus incorporated in the manufacturing system in FIG. 1.

FIG. 3 schematically illustrates a basis weight measuring apparatus 16 for the sheet tobacco ST.

The basis weight measuring apparatus 16 measures a basis weight of the sheet tobacco ST in a course of the sheet tobacco ST subjected to the drying processing being transported on a transport path 18.

The transport path 18 includes a net conveyer 20 as an upstream section extending from the dryer, and a downstream section 21 disposed with a predetermined space, that is, clearance between the downstream section 21 and a downward end of the net conveyer 20, and in the present embodiment, the downstream section 21 includes a cutter 22 at an upstream end thereof. The cutter 22 includes a plurality of rotary knives, and cuts the sheet tobacco ST into a plurality of sheet tobacco webs along a direction of the transport of the sheet tobacco ST.

The transport path 18 further includes a transport guide plate 24 for the clearance, that is, connecting the net conveyer 20 and the cutter 22, and the transport guide plate 24 extends horizontally along the transport path 18 and guides the transport of the sheet tobacco ST.

The basis weight measuring apparatus 16 has a measurement position P on the transport guide plate 24, and in the transport guide plate 24, an aperture 26 is formed at the measurement position P. The aperture 26, for example, has a round shape, and has an axis A perpendicular to the transport guide plate 24.

The basis weight measuring apparatus 16 includes a light source 28, and the light source 28 is disposed below the transport guide plate 24 and emits light through the aperture 26 toward the sheet tobacco ST on the transport guide plate 24.

Meanwhile, the basis weight measuring apparatus 16 further includes a visual sensor 30, and the visual sensor 30 has, for example, a CCD-type color camera 32. The color camera 32 is disposed on the axis A of the aperture 26, that is, disposed so as to directly face the aperture 26, and as indicated by arrow V in FIG. 3, the color camera 32 is movable in a direction along the axis A. Therefore, a focus of a lens in the color camera 32 can be adjusted by moving the color camera 32 along the axis A, enabling the color camera 32 to be easily positioned above an upper surface of the sheet tobacco ST passing through the aperture 26.

As is clear from FIG. 3, the light source 28 is not disposed on the axis A, but is disposed to deviate, for example, downstream of the axis A as viewed in the direction of the transport of the sheet tobacco ST, and a predetermined distance is secured between the axis A and the light source 28. In other words, if a projection region in which the aperture 26 is projected on a horizontal plane on which the light source 28 is disposed is considered, the light source 28 is disposed off the projection region for the aperture 26. Here, the light source 28 may be disposed to deviate in the direction across the transport path 18 with respect to the projection region.

An optical axis L of the light source 28 is not parallel with the axis A, but is inclined relative to the axis A. Therefore, light emitted from the light source 28 is directed to the sheet tobacco ST through the aperture 26. The light passes through the sheet tobacco ST, but the passing light does not directly enter the color camera 32.

In particular, in the case of a rolled sheet tobacco ST formed by the roll forming machine described above, small through holes are formed in a distributed manner in a surface of the rolled sheet tobacco ST. Therefore, even if light emitted from the light source 28 passes through such through holes, the passing light does not directly enter the color camera 32. In other words, a configuration in which the optical axis L of the light source 28 is disposed off the axis A is effective for preventing emitted light from directly entering the color camera 32.

On this point, if the sheet tobacco ST is not a rolled sheet tobacco but a papermaking method-used sheet tobacco, no through holes such as mentioned above exist in the papermaking method-used sheet tobacco, and it is not necessary to take direct entrance of emitted light to the color camera 32 into consideration and thus the light source 2.8 may be disposed on the axis A. Note that a papermaking method-used sheet tobacco is manufactured using fibrous tobacco and a paper-making method.

Furthermore, the light source 28 includes an air nozzle 34, and the air nozzle 34 is connected to a compressed air source 36. The air nozzle 34 provides a blow of compressed air along a flat light emission surface of the light source 28. Such air blow suppresses deposition of dust on the light emission surface and thereby reduces the number of cleanings of the light emission surface.

Figure 4:
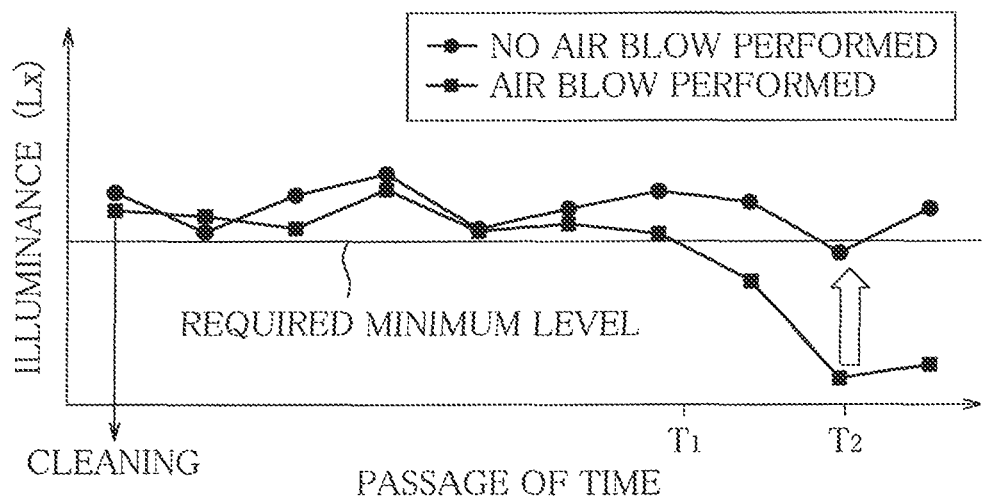
FIG. 4 is a graph indicating changes in illuminance of sheet tobacco over time.

FIG. 4 illustrates temporal changes in illuminance of light emitted from the light source 28 to the sheet tobacco ST. If no air blow is performed, the illuminance falls below the required minimum level when the time passed from cleaning of the light emission surface reaches to T1. On the other hand, if air blow is performed, the illuminance falls below the required minimum level when the time passed from the cleaning of the light emission surface reaches to T2, which is longer than T1.

The color camera 32 periodically photographs the sheet tobacco ST passing through the measurement position P, that is, the aperture 26 to obtain a color image of the sheet tobacco TS.

Here, when the color image is taken, the sheet tobacco ST is supported on the transport guide plate 24, whereby a fixed distance between the color camera 32 and the sheet tobacco ST is maintained, enabling the color camera 32 to obtain a favorable color image.

Also, since the light source 28 is disposed in such a manner as described above, even if a plurality of small through holes exist in the sheet tobacco ST, as described above, the emitted light does not directly enter the color camera 32. Accordingly, the color camera 32 can obtain a favorable color image of the sheet tobacco ST without halation.

On this point, an inverted layout of the light source 28 and the color camera 32, which is opposite to the above-described preferable layout is possible, and in this inverted layout, the light source 28 is disposed so as to directly face the aperture 26 while the color camera 32 is disposed off the axis A of the aperture 26 and obliquely inclined relative to the axis A. Such inverted layout also enables avoidance of direct entrance of the light to the color camera 32.

However, the color camera 32 in this inverted layout receives light passed obliquely relative to a thickness direction of the sheet tobacco ST, and an attenuation ratio of the light received by the color camera 32 is high, and this attenuation ratio increases as the inclination of the color camera 32 is larger. Thus, the color camera 32 does not obtain a color image reflecting the thickness of the sheet tobacco ST.

On the other hand, the color camera 32 in the preferable layout receives light passed through the sheet tobacco ST in the thickness direction of the sheet tobacco ST, enabling a color image reflecting the thickness of the sheet tobacco ST.

The visual sensor 30 further includes a calculation section electrically connected to the color camera 32, that is, a basis weight calculation unit 38, and the basis weight calculation unit 38 receives a color image of the sheet tobacco ST taken via the color camera 32, and calculates a basis weight of the sheet tobacco ST based on the color image.

Figure 5:
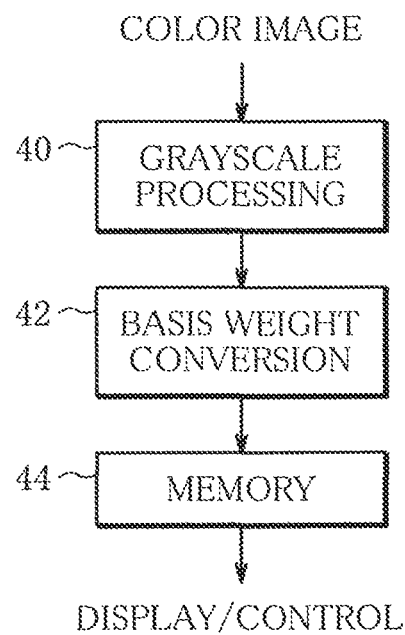
FIG. 5 is a block diagram illustrating details of the basis weight measuring part in FIG. 3.

As illustrated in FIG. 5, the basis weight calculation unit 38 includes a transformer that transforms a color image into a 256-shade grayscale image, that is, what is called a grayscale processing part 40. Each pixel of the grayscale image has a pixel value expressed by an average value of an R component (red), a G component (green) and a B component (blue) of a corresponding pixel in the color image. Furthermore, the grayscale processing part 40 performs an arithmetic operation to obtain an average gray level of the grayscale image based on the pixel values of the respective pixels in the grayscale image and outputs the average gray level.

The average gray level is sent from the grayscale processing part 40 to a basis weight conversion part 42, and converted into a basis weight of the sheet tobacco ST by the basis weight conversion part 42. More specifically, the basis weight conversion part 42 has the conversion map X illustrated in FIG. 6 in advance, and the conversion map X indicates a correlation between average gray level obtained from a grayscale image of sheet tobacco ST and basis weight of sheet tobacco ST in the form of a linear function.

In order to obtain such conversion map X, a plurality of test pieces of sheet tobacco are prepared and these test pieces have known basis weights that are different from one another. Average gray levels of these test pieces are calculated using the above-described visual sensor 30, and therefore, the conversion map X can be obtained by relating the calculated average gray levels and the basis weights of the test pieces to each other. Here, the present inventors have confirmed that a contribution ratio (accuracy) of the average gray levels relative to the actual basis weights is no less than 90%.

Figure 6:
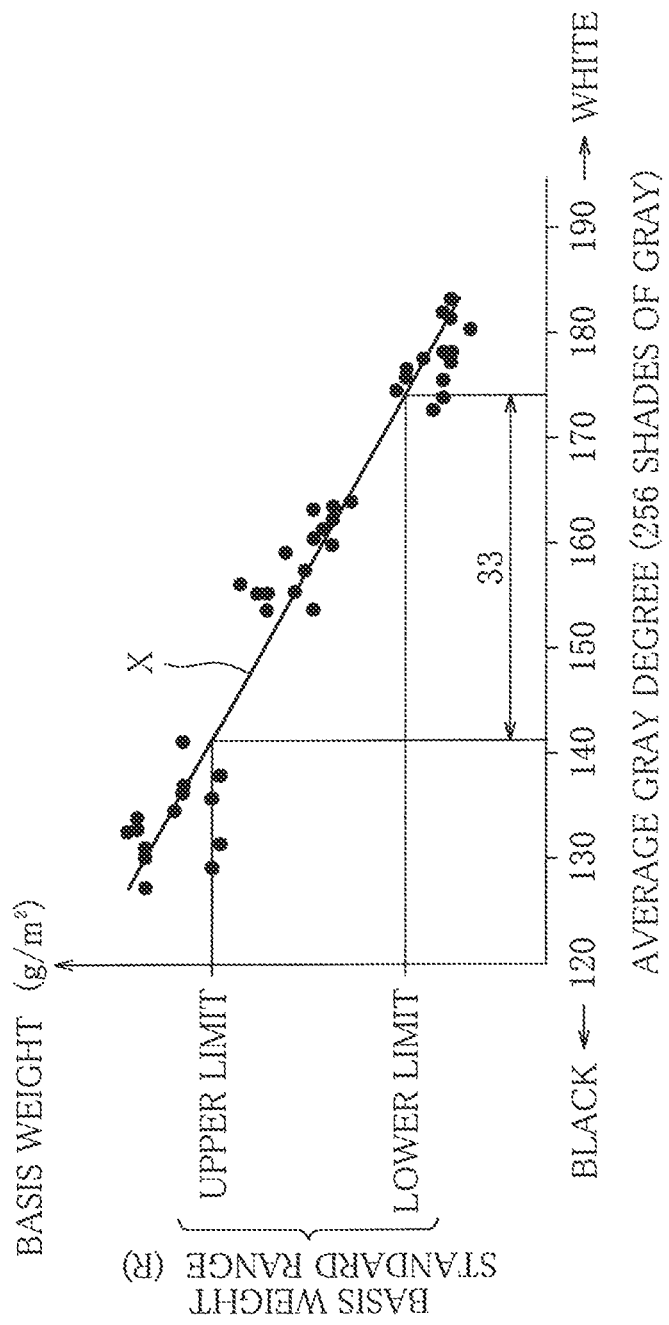
FIG. 6 is a graph indicating a conversion map included in the basis weight conversion part in FIG. 5.

Therefore, if the conversion map X illustrated in FIG. 6 is prepared in advance, the basis weight conversion part 42 can calculate a correct basis weight of the sheet tobacco ST by reading a basis weight corresponding to a calculated average gray level from the conversion map X.

Subsequently, the calculated basis weight is stored in a memory 44 while calculated basis weight is sent from the basis weight calculation unit 38 to each of the display device 45 and the control device 46. The display device 45 displays the calculated basis weight together with data such as a machine number of the roll forming machine and a time of the measurement.

Figure 7:
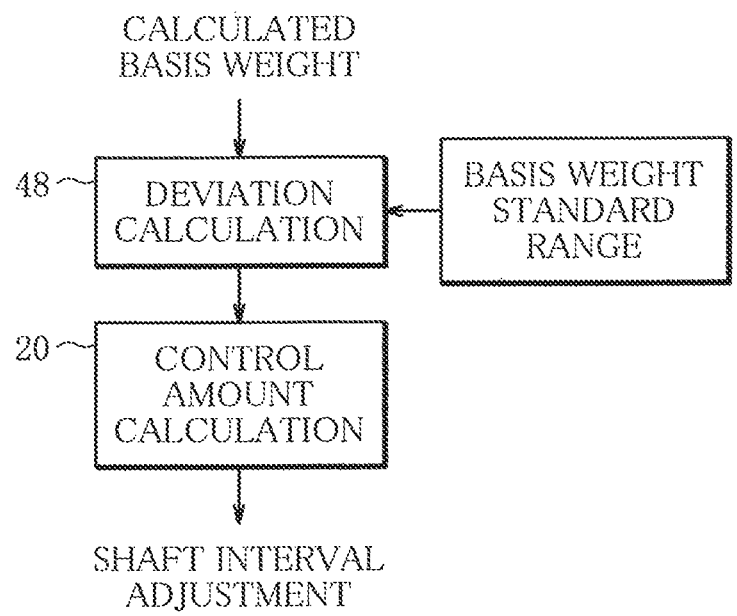
FIG. 7 is a block diagram illustrating details of the control device in FIG. 3.

The control device 46 determines whether the basis weight is acceptable or not and controls the actuation of the above-described shaft interval adjustment device 14 based on a result of the determination. For example, as illustrated in FIG. 7, the control device 46 includes a deviation calculation part 48, and the calculated basis weight calculated by the basis weight calculation unit 38 and a basis weight standard range R are provided to the deviation calculation part 48.

Here, the basis weight standard range R is defined by the following expression where Wb is a standard basis weight required for sheet tobacco ST.

$$R = Wb \pm \alpha$$

Here, $\alpha$ indicates an allowable margin relative to the standard basis weight Wb.

Referring to FIG. 6, a relationship between the basis weight standard range R and the above-described conversion map X is more clearly indicated. In the present embodiment, a range of 33 shades of gray (gradation) is secured in terms of 256-level grayscale between average gray levels corresponding to an upper limit and a lower limit of the basis weight standard range R, respectively, and thus the basis weight standard range R has a range of shades of gray that constitutes approximately 13% of a sensor span (256 shades of gray) of the visual sensor 30. This means that the visual sensor 30 in the present embodiment can more precisely calculate a basis weight of sheet tobacco ST.

The deviation calculation part 48 calculates deviation of the calculated basis weight from the standard range R and sends the deviation to a control amount calculation part 50. The control amount calculation part 50 calculates an amount of control of the gap G to be performed by the above-described shaft interval adjustment device 14 based on the deviation and provides the control amount to the shaft interval adjustment device 14. Therefore, the shaft interval adjustment device 14 adjusts the gap G according to the control amount, and as a result, the basis weight of the sheet tobacco ST to be formed is maintained within the standard range R, enabling avoidance of manufacture of defective sheet tobacco ST.

The above-described visual sensor 30 may include a plurality of color cameras 32, and in this case, these color cameras 32 are disposed with a space in a width direction of the sheet tobacco ST therebetween. However, use of a single color camera 32 alone causes no trouble in calculating a basis weight of the sheet tobacco ST.

Figure 8:
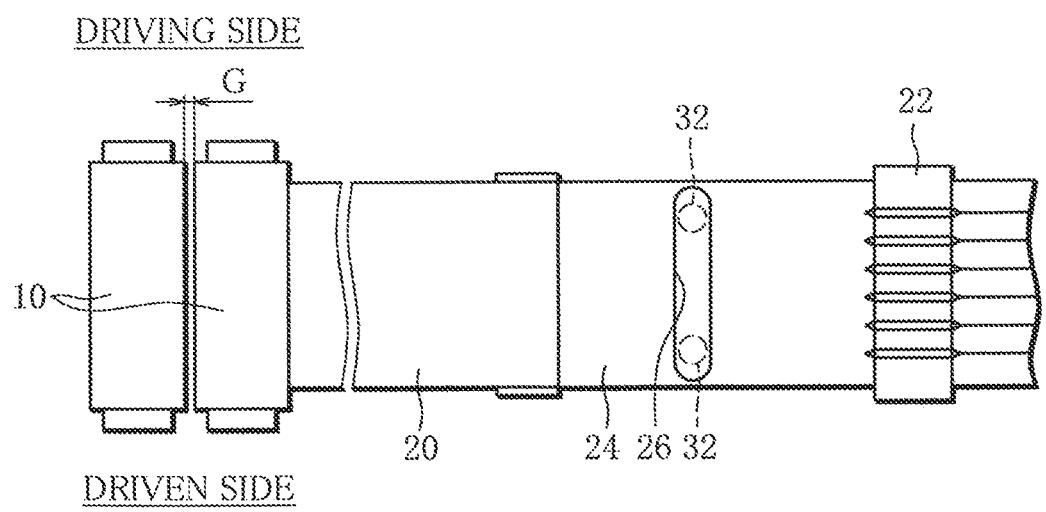
FIG. 8 is a diagram illustrating an example in which a pair of color cameras is separately disposed on the driving side and the driven side of a pair of press rolls.

In order to demonstrate this, as illustrated in FIG. 8, a pair of color cameras 32 was prepared, and these color cameras 32 were separately disposed on the driving side and the driven side of the pair of press rolls 10 in an axis direction of the pair of press rolls 10 (width direction of the sheet tobacco ST) and used for measurement of basis weight of the sheet tobacco ST.

Here, the driving side of the press rolls 10 means one end side of roll shafts from which respective driving forces are inputted to the press rolls 10, and the driven side of the press rolls 10 means another end side of the roll shafts.

Figure 9:
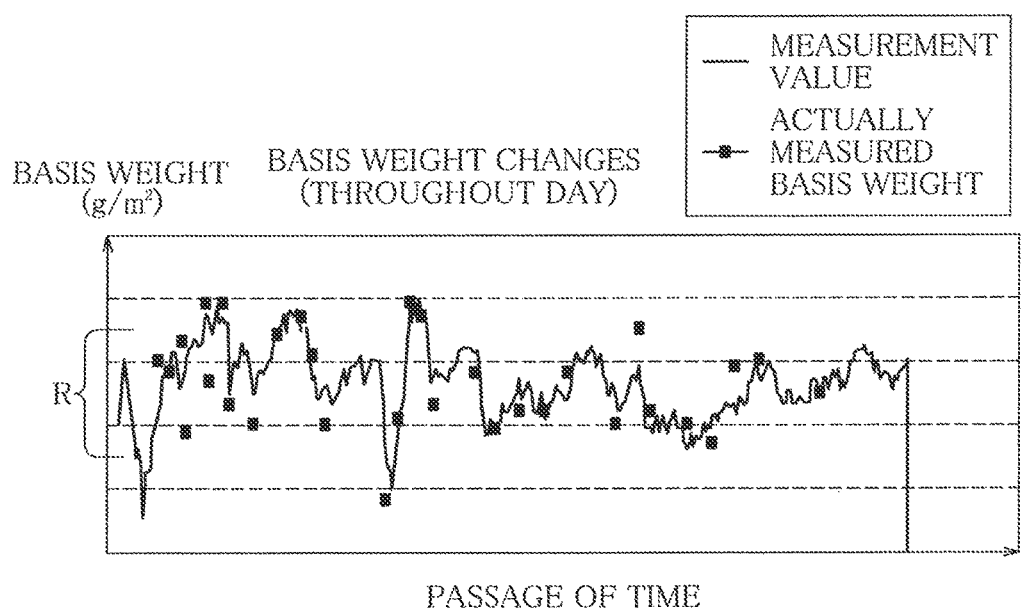
FIG. 9 is a graph indicating a relationship between the basis weight of the sheet tobacco measured using the color camera on the driving side and the passage of time.

FIG. 9 illustrates temporal change in each of basis weight measurement value and actually measured basis weight of the sheet tobacco ST, and it was confirmed that each of these temporal changes has a similar tendency regardless of the driving side and the driven side. Therefore, as is clear from FIG. 9, there is no large difference in basis weight between the drive side and the driven side of the sheet tobacco ST. Therefore, even use of a single color camera 32 enables effective measurement of a basis weight of sheet tobacco ST and thus enables provision of the basis weight measuring apparatus according to the present invention at a low cost.

Figure 10:
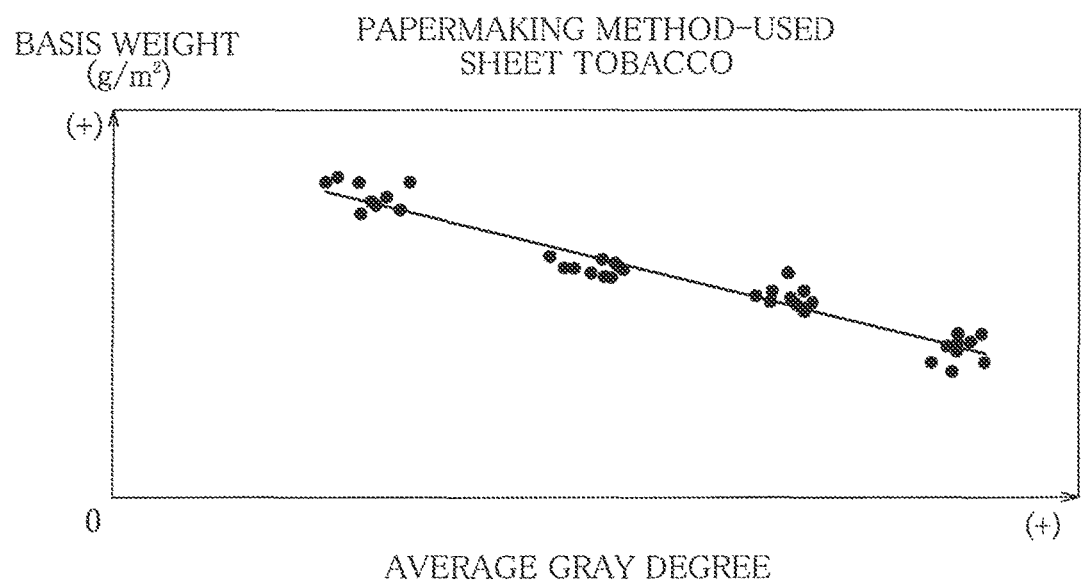
FIG. 10 is a graph indicating a relationship between basis weight of papermaking method-used sheet tobacco and average gray level of papermaking method-used sheet tobacco measured using a color camera.

Although the above-described embodiment is applied to measurement of a basis weight of sheet tobacco formed by rolling, it should be understood that the present invention is applicable also to measurement of a basis weight of papermaking method-used sheet tobacco. FIG. 10 illustrates a relationship between average gray level and basis weight of papermaking method-used sheet tobacco, and as is clear from FIG. 10, the average gray level is in proportion to the basis weight also in the case of papermaking method-used sheet tobacco.

Furthermore, the color camera and the transport guide plate are not essential for carrying out the present invention. For example, a monochrome camera can be used instead of the color camera. Also, if no transport guide plate is used, a light source and a camera are disposed with the aforementioned clearance as an aperture, in the transport path 18 therebetween.

EXPLANATION OF REFERENCE SIGNS 10 press roll
14 shaft interval adjustment device
16 basis weight measuring apparatus
18 transport path
20 mesh conveyer (upstream section)
21 downstream section
24 transport guide plate
26 aperture
28 light source
30 visual sensor
32 color camera
34 air nozzle
38 basis weight calculation unit
40 grayscale processing part (transformer)
42 basis weight conversion part (converter)
44 memory
45 display device
46 control device
A axis
P measurement position
R basis weight standard range
ST sheet tobacco

The invention claimed is:

1. A basis weight measuring apparatus for sheet tobacco, the apparatus comprising:
a light source disposed on a transport path for the sheet tobacco, and emitting light toward the sheet tobacco passing through a measurement position defined in the transport path, the transport path including an aperture therein and allowing the sheet tobacco passing through the measurement position to be exposed to the light source, the aperture having an axis perpendicular to the transport path; and
a visual sensor including:
a camera disposed with the transport path put between said visual sensor and said light source, said visual sensor measuring a basis weight of the sheet tobacco based on an image of the sheet tobacco taken by the camera when the sheet tobacco passes through the measurement position;
a calculation section calculating an average gray level of the image and outputting the average gray level; and
a converter having a conversion map indicating a relationship between the average gray level and an actual measurement value obtained by actually measuring the basis weight of the sheet tobacco, the converter converting the average gray level into the basis weight of the sheet tobacco with reference to the conversion map,
wherein the camera is disposed on the axis of the aperture while the light source is disposed to deviate from the aperture in a direction along the transport path or a direction across the transport path.

2. The basis weight measuring apparatus for sheet tobacco according to claim 1, wherein the camera is a color camera that obtains the image as a color image, and
wherein the calculation section has a transformer that transforms the color image into a grayscale image, and calculates the average gray level based on the grayscale image.

3. The basis weight measuring apparatus for sheet tobacco according to claim 1, wherein the transport path further includes:
an upstream section that transports the sheet tobacco toward the measurement position; and
a downstream section disposed with a clearance, in which the measurement position is defined, interposed between the downstream section and a downstream end of the upstream section, the downstream section transporting the sheet tobacco passing through the measurement position,
wherein said light source and the camera are disposed with the clearance put therebetween.

4. The basis weight measuring apparatus for sheet tobacco according to claim 3, wherein the transport path further includes a transport guide plate disposed in the clearance, and guiding transport of the sheet tobacco when the sheet tobacco moves from the upstream section toward the downstream section through the measurement position, and
wherein the aperture is formed in the transport guide plate.

5. The basis weight measuring apparatus for sheet tobacco according to claim 1, wherein the sheet tobacco is rolled sheet tobacco.

6. The basis weight measuring apparatus for sheet tobacco according to claim 1, wherein said light source has an optical axis inclined relative to the axis of the aperture.

7. A basis weight measuring method for sheet tobacco, the method comprising:
emitting light toward the sheet tobacco passing through a measurement position defined on a transport path, from a light source in a course of transport of the sheet tobacco along the transport path, the transport path including an aperture therein and allowing the sheet tobacco passing through the measurement position to be exposed to the light source, the aperture having an axis perpendicular to the transport path;
obtaining an image of the sheet tobacco passing through the measurement position using a camera disposed with the transport path put between the camera and the light source;
calculating an average gray level of the image; and converting the average gray level into a basis weight of the sheet tobacco with reference to a conversion map prepared in advance, the conversion map indicating a relationship between the average gray level and an actual measurement value obtained by actually measuring the basis weight of the sheet tobacco, wherein the camera directly faces the aperture and takes the image of the sheet tobacco while the light source emits the light to the sheet tobacco through the aperture from a position deviated from the aperture.

8. The basis weight measuring method for sheet tobacco according to claim 7, wherein the image is a color image obtained using a color camera, and wherein the average gray level is calculated based on a grayscale image resulting from transformation of the color image.

9. The basis weight measuring method for sheet tobacco according to claim 7, wherein the sheet tobacco passing through the measurement position is guided on a transport guide plate and receives the light emitted from the light source through the aperture formed in the transport guide plate.

10. The basis weight measuring method for sheet tobacco according to claim 9, wherein the sheet tobacco is rolled sheet tobacco.

11. The basis weight measuring method for sheet tobacco according to claim 7, wherein the light source obliquely emits the light to the sheet tobacco through the aperture.

12. A manufacturing system for sheet tobacco, the system comprising:

a forming machine provided upstream of a basis weight measuring apparatus according to claim 1, for forming sheet tobacco and sending the manufactured sheet tobacco out onto the transport path, said forming machine including an adjustment device for adjusting a basis weight of sheet tobacco to be manufactured; and a control device for controlling the adjustment device based on a basis weight measurement result obtained by the basis weight measuring apparatus and a standard basis weight range for sheet tobacco.

13. A manufacturing method for sheet tobacco, the method comprising:

manufacturing sheet tobacco prior to measurement of a basis weight of the sheet tobacco by a basis weight measuring method according to claim 7;

sending the manufactured sheet tobacco out onto the transport path; and controlling a basis weight of sheet tobacco to be manufactured, based on a basis weight measurement result obtained by the basis weight measuring method and a standard basis weight range for sheet tobacco.

* * * * *